United States Patent [19]
Althin et al.

[11] Patent Number: 5,643,452
[45] Date of Patent: Jul. 1, 1997

[54] HIGH-FLUX HOLLOW-FIBER MEMBRANE WITH ENHANCED TRANSPORT CAPABILITY AND PROCESS FOR MAKING SAME

[75] Inventors: Anders Althin, Miami Lakes; Ben Fernandez, Miami; Raymond Elsen, Miami Lakes; Kees Ruzius, Miami; Lalith Silva, Miami Lakes; George Washington, Miami, all of Fla.

[73] Assignee: Althin Medical, Inc., Miami, Fla.

[21] Appl. No.: 327,431

[22] Filed: Oct. 21, 1994

Related U.S. Application Data

[63] Continuation of Ser. No. 976,949, Nov. 16, 1992, abandoned.

[51] Int. Cl.$^6$ .................................................. B01D 71/16
[52] U.S. Cl. ............................... 210/500.23; 210/500.3; 264/41
[58] Field of Search .......................... 210/500.23, 490, 210/651, 646, 500.3; 364/41, 49, 200, 209.1

[56] References Cited

U.S. PATENT DOCUMENTS

| | | | |
|---|---|---|---|
| 4,276,173 | 6/1981 | Kell et al. | 210/500.23 |
| 4,543,221 | 9/1985 | Chen et al. | 264/41 |
| 4,781,833 | 11/1988 | Mizutani et al. | 210/321.81 |

OTHER PUBLICATIONS

*First Annual Progress Report: Research on Improved Hollow Fiber Artificial Kidney*, NIH Contract No. NIH–NIAMDD/70–2302, Nov. 1, 1971.
*Second Annual Progress Report: Research on Improved Hollow Kidney*, NIH Contract No. NIH–NIAMDD/70–2302, Dec. 31, 1972.
*Third Annual Progress Report: Studies on the Molecular Etiology of Uremia Using High Flux Cellulose Acetate Dialyzers*, NIH Contract No. NIH–NIAMDD/70–2302, Aug. 15, 1973.
*Final Report: Research on Improved Hollow–Fiber Artificial Kidney*, NIH Contract No. NIH–NIAMDD/70–2302, Dec. 31, 1973.
Marketing Literature for DUO–FLUX® Cellulose Acetate Hemodialyzer, Althin CD Medical, Inc. (Date unknown, but believed to be before filing date of subject application).
Proceedings of Second Annual Contractors' Conference of the Artificial Kidney Program of the National Institute of Arthritis and Metabolic Diseases, Held Jan. 22–24, 1969, pp. 69–70.

*Primary Examiner*—Frank Spear
*Attorney, Agent, or Firm*—Klarquist Sparkman Campbell Leigh & Whinston, LLP

[57] ABSTRACT

Semipermeable membranes are disclosed for purifying aqueous biological fluids. The membranes are particularly suitable for purifying extracorporeal blood via hemodialysis. The membranes, preferably configured as hollow fibers, are made from a hydrophilic polymeric material, preferably cellulose acetate. Features of the membranes include an ultrafiltration coefficient ($K_{uF}$) of about 15 to about 55 mL/hr/mmHg/m$^2$ (thus termed "high-flux" type membranes), a urea mass transfer coefficient ($K_{ov}$(urea)) of at least $38 \times 10^{-3}$ cm/min, and a ratio of $K_{ov}$(urea)/$K_{uF}$ of at least $2.5 \times 10^{-3}$. Hollow fibers of such membranes suitable for hemodialysis have a lumen diameter of about 175 to about 210 µm and a wall thickness of about 10 to about 35 µm. According to disclosed methods for making the membranes, a melt comprising about 32 to about 40% w/w cellulose acetate, about 5 to about 10% w/w glycerine, and about 50 to about 67% w/w polyethylene glycol is extruded to make hollow fibers; the fibers are cooled, cold-stretched, water-leached, and replasticized using a glycerine solution.

16 Claims, 5 Drawing Sheets

HIGH-FLUX HOLLOW-FIBER MEMBRANE WITH ENHANCED TRANSPORT CAPABILITY AND PROCESS FOR MAKING SAME

This is a continuation of application Ser. No. 07/976,949, filed Nov. 16, 1992, now abandoned.

BACKGROUND OF THE INVENTION

While semipermeable membranes that are useful for purifying aqueous biological fluids and made according to the prior art have features that are advantageous for certain applications, they nonetheless have certain limitations. The present invention seeks to overcome certain drawbacks of prior-art membranes and to provide new features not heretofore available.

A discussion of the features and advantages of the present invention is deferred to the following detailed description, which proceeds with reference to the accompanying drawings.

DETAILED DESCRIPTION

The present invention provides semipermeable hollow-fiber membranes having a novel combination of hydraulic (i.e., water) permeability and diffusive (i.e., solute) permeability. With respect to diffusive permeability, the membranes according to the present invention are permeable to solutes normally present in aqueous biological fluids (such as blood) having molecular weights up to 30,000 daltons and higher. Thus, the membranes provide optimum operating characteristics when used in separation processes or blood purification applications.

This invention also encompasses processes for making cellulose acetate fibers having the above-specified characteristics.

The fibers according to the present invention preferably comprise a hydrophilic polymeric material of a thermoplastic nature, most preferably cellulose acetate. For use in processing biological fluids, the hydrophilic polymeric material preferably also is resistant to thrombogenesis, and is non-toxic. It has been found that cellulosic polymers are particularly well-adapted for such use.

In order to form membranes with the requisite hydraulic and diffusive permeability characteristics, the hydrophilic polymeric material is liquified (i.e., melted) and combined with a water-miscible solvent for the hydrophilic polymeric materials and a water-miscible non-solvent for the hydrophilic polymeric material. Of course, the solvent and the non-solvent must be liquids at the melt temperature of the hydrophilic polymeric material. Also, the solvent and the non-solvent are preferably non-toxic and resistant to thrombogenesis. The resulting mixture is mixed to homogeneity and "melt-spun" (i.e., extruded in a molten condition) through an annular extrusion die.

As discussed below, the mixture can be melt-spun twice, once using a die suitable for making solid fibers, then again using an annular die to produce hollow fibers. Spinning twice allows superior control over the composition and characteristics of the hollow fibers.

After extrusion, the resulting hollow fibers are rapidly cooled to solidify their constituent materials and leached in heated water to remove the solvent and the non-solvent.

In the melt, molecules of the solvent and non-solvent constituents are homogeneously interspersed with molecules of the hydrophilic polymeric material. During extrusion and subsequent cooling, the molecules of the hydrophilic polymeric material undergo a degree of thermodynamic ordering of themselves relative to the solvent and non-solvent constituents. (This process is termed a "thermally-induced phase separation process," abbreviated "TIPS.") As a result, the molecules of the hydrophilic polymeric material become associated with each other during spinning to form a labyrinthine network that, after the solvent and non-solvents are removed by water leaching, is characterized by an extensive and dense network of convoluted voids having an extremely fine mean pore size. These voids extend through the walls of the hollow fibers and provide the routes by which water and solutes pass through the walls. The molecules of the solvent and non-solvent, which originally occupied the voids, are removed by the water-leach step because they are miscible in water and because they do not become covalently bonded to the molecules of the hydrophilic polymeric material.

For example, and not intended to be limiting, a cellulose acetate hollow fiber according to the present invention is made from a composition comprising a mixture of three constituents. A first constituent is the cellulose acetate polymer which provides the structural aspect of the membrane. A second constituent is glycerine, a non-solvent for cellulose at ambient temperature. A third constituent is polyethylene glycol, a solvent for cellulose at ambient temperature. A preferred mixture for making cellulose acetate membranes consists essentially of about 32 to about 40 percent (w/w) cellulose acetate, about 5 to about 10 percent (w/w) glycerin, and the balance polyethylene glycol having a molecular weight in a range of about 150 to about 600 daltons.

A process for making cellulose acetate membranes according to the present invention typically includes a "compounding" step in which the three compounds are mixed to homogeneity at a temperature appropriate to melt cellulose acetate (about 165° to about 180° C.). The resulting first "melt" is then extruded through a die to form solid strands. The strands are cooled and pelletized using conventional methods. The composition of the pellets is substantially the same as the composition of the first melt. These procedural steps are also generally applicable to producing a first melt of other hydrophilic polymeric materials according to the present invention and to extruding the first melt.

Fabrication of hollow-fiber membranes from the pellets is performed by first heating the pellets sufficiently to form a second "melt" which is extruded through an annular spinneret. The resulting hollow fibers are immediately cooled by air and leached in a water bath at a temperature of about 80° to about 95° C.

The temperature of the second melt while being extruded through the annular spinneret is a key parameter affecting the hydraulic permeability of the resulting membrane. For example, with respect to cellulose acetate, each one degree Celsius increase in spin temperature causes a corresponding decrease in the hydraulic permeability of the hollow fiber by about 2 mL/min/mmHg/m². Thus, it is possible to "customize" the hydraulic permeability of the hollow fibers by simply controlling the spin temperature.

It is also important that the conditions under which the hollow fibers are cooled upon exiting the annular spinneret be maintained substantially constant to ensure uniform fiber characteristics over the length of the fiber produced by the spinneret. These conditions include, but are not necessarily limited to, the temperature of the air used to cool the fiber, the velocity of air movement past the fiber exiting the spinneret, the longitudinal tension applied to the fiber as it exits the spinneret, the rate at which the fiber is cooled relative to the longitudinal velocity of the fiber as it exits the spinneret, and the humidity of the air used to cool the fiber. The longitudinal tension should be sufficient to longitudinally stretch the fiber by no greater than twenty percent.

In the water bath, the glycerin and polyethylene glycol constituents of the follow fibers are leached from the polymeric constituent. After leaching, the hollow fibers are taken up in a wet condition on reels. The wet fibers possess excellent hydraulic and diffusive permeability characteristics with high solute clearances for middle and high molecular weight substances while still exhibiting a manageable ultrafiltration rate for use in hemodialyzers and the like.

In the "pores" of the wet fibers water molecules essentially replace the molecules of solvent and non-solvent leached away by the water. Thus, the water molecules contribute a substantial degree of structural integrity to the fibers which would otherwise collapse and thereby lose their desired hydraulic and diffusive permeability characteristics.

However, it is impractical to maintain the fibers in such a wet condition for extended periods or to incorporate "wet" fibers into such appliances as hemodialyzers using available methods. Therefore, it is necessary to ultimately replace a substantial portion of the water with a stabilizing substance that is resistant to evaporation under ambient conditions but does not interfere with downstream steps necessary to incorporate the fibers into a useful appliance. Such a water-replacement step is termed "replasticization."

For example, wet cellulose acetate fibers are preferably replasticized using a solution of glycerin and water. The wet fibers are unreeled and submerged at about 25° C. in an aqueous glycerin solution having a glycerin concentration of about 30 to about 40% w/w. The fibers are subsequently dried using air heated to about 70° to about 80° C. After drying, the cellulose acetate fibers can remain stable for extended periods of time because the "plasticizer" (i.e., glycerin and some water) is in equilibrium with the atmosphere at ambient temperature and humidity. At equilibrium, the concentration of glycerin in the cellulose acetate membrane is about 45 to about 50% w/w and the water content is about 15 to about 18% w/w.

Hollow cellulose acetate fibers according to the present invention can be made into hollow-fiber hemodialyzers using methods known in the art. When made into hemodialyzers, such fibers have been shown to have the following specifications:

| | |
|---|---|
| Fiber internal diameter: | about 175 to about 210 µm |
| Fiber wall thickness: | about 10 to about 35 µm |
| Ultrafiltration coefficient ($K_{UF}$) | about 15 to about 55 mL/hr/mmHg/m² |
| Mass-transfer coefficient for urea ($K_{oV}$ (urea)) | about $38 \times 10^{-3}$ cm/min or higher |
| Ratio of [$K_{oV}$ (urea)]/$K_{UF}$ | at least $2.5 \times 10^{-3}$ |

Representative instructions for preparing a hemodialyzer according to the present invention for use in a hemodialysis procedure are set forth in Appendix A.

A representative clinical monitoring protocol for evaluating a hemodialyzer according to the present invention is set forth in Appendix B.

EXAMPLE 1

This Example is an investigation of the effects of cellulose acetate concentration and hot water-bath leach temperature on diffusive ($K_{oV}$) and hydraulic ($K_{UF}$) permeability values of hollow-fiber membranes according to the present invention. Results are shown in Table 1.

TABLE 1

| [Cellulose Acetate] (% w/w) | 65° C. Leach $K_{oV}$ (Urea) (cm/min) | Bath $K_{UF}$* | 75° C. Leach $K_{oV}$ (Urea) (cm/min) | Bath $K_{UF}$* |
|---|---|---|---|---|
| 42.8 | $35.3 \times 10^{-3}$ | 7.6 | $37.7 \times 10^{-3}$ | 10.2 |
| 40.3 | $33.9 \times 10^{-3}$ | 9.0 | — | — |
| 38.3 | $37.3 \times 10^{-3}$ | 13.3 | $41.6 \times 10^{-3}$ | 19.8 |
| 38.3 | $36.8 \times 10^{-3}$ | 13.3 | $43.4 \times 10^{-3}$ | 18.4 |
| 36.7 | $38.2 \times 10^{-3}$ | 18.2 | $45.0 \times 10^{-3}$ | 25.6 |
| 34.6 | $41.0 \times 10^{-3}$ | 24.4 | $46.9 \times 10^{-3}$ | 31.1 |
| 32.9 | $42.7 \times 10^{-3}$ | 27.4 | $47.9 \times 10^{-3}$ | 36.1 |

*units: mL/hr/mmHg/m²

EXAMPLE 2

This Example illustrates the effect of leach-bath temperature on the diffusive permeability ($K_{oV}$) and hydraulic permeability ($K_{UF}$) of cellulose acetate hollow fibers having a preferred cellulose acetate content of 34.5% w/w. Results are shown in Table 2.

TABLE 2

| Bath Temp °C. | $K_{oV}$ (Urea) cm/min | $K_{UF}$ (mL/hr/mmHg/m²) |
|---|---|---|
| 75 | $52.1 \times 10^{-3}$ | 27.8 |
| 80 | $50.0 \times 10^{-3}$ | 29.4 |
| 85 | $49.6 \times 10^{-3}$ | 36.4 |

EXAMPLE 3

This Example illustrates the effects of compounding temperature and hollow-fiber melt-spin temperature on the diffusive and hydraulic permeability values of hollow fibers comprising 34.5% w/w cellulose acetate after passing through an 85° C. leach bath. Results are shown in Table 3.

TABLE 3

| Compounding Temp (°C.) | Fiber Spin Temp (°C.) | $K_{ov}$ (Na) (cm/min) | $K_{UF}$ (mL/hr/mmHg/m²) |
| --- | --- | --- | --- |
| 165.6 | 172.2 | $45.7 \times 10^{-3}$ | 56.1 |
| 168.3 | 175 | $45.7 \times 10^{-3}$ | 52.2 |
| 171.1 | 175 | $51 \times 10^{-3}$ | 32.4 |
| 173.8 | 175 | $49.6 \times 10^{-3}$ | 36.5 |
| 176.7 | 177.2 | $44.5 \times 10^{-3}$ | 29.2 |

EXAMPLE 4

This Example is an investigation of sieving behavior of hollow-fiber membranes according to the present invention compared with prior-art hollow-fiber membranes. The sieving statistics were determined using maltodextrin solutions. See generally, Feldhoff et al., "Effect of Plasma Proteins on the Sieving Spectra of Hemofilters," *Artif. Organs* 8:186–192 (1984).

Cellulose acetate hollow fibers made according to the present invention were bundled and made into hollow-fiber hemodialyzers using conventional procedures.

The lumens of the hollow fibers (i.e., the "blood" side of the semi-permeable membrane represented by the fibers) received either a human plasma containing maltodextrin or a saline rinse. The maltodextrin used in this study had a continuous distribution of molecular weights from about 350 daltons (maltose) to greater than 120,000 daltons. Normal dialysate at 37° C. as used in hemodialysis was used in the "dialysate" side.

Three liters of human plasma recovered from whole blood were heated to 60° C. for 30 minutes to destroy dextrinases. Any cryoprecipitate and coagulated proteins produced by heating the plasma in this matter were removed by centrifuging the plasma at 10,000×g for 30 minutes. Maltodextrin was then added to a concentration of 6% w/w. The temperature of the plasma-maltodextrin solution was maintained at 37° C. with slow stirring using a water bath.

For saline rinses of the fiber lumens, one liter of normal saline was prepared and likewise maintained at 37° C.

Delivery of plasma or normal saline through the lumens, and delivery of dialysate, were accomplished using conventional peristaltic pumps, with tubing lengths from the respective reservoirs to the dialyzer and back being less than one meter each way. The "plasma" pump was adjusted to deliver plasma or saline to the arterial blood port of the dialyzer at 200 mL/min with a slight back pressure on the venous blood port. The "dialysate" pump was coupled to the dialysate port of the dialyzer with the downstream dialysate port plugged. The dialysate pump was run at 30 mL/min.

Pressure transducers were connected by tubing and "T" connections to the arterial blood port, the venous blood port, and the upstream dialysate port. All pressure-monitoring components were positioned at the same hydrostatic elevation to avoid pressure differentials.

Before being connected as described above, the dialyzers were rinsed, by "cross-membrane" flow, with one liter of normal saline under a hydrostatic pressure of one meter to wash out glycerine and other solutes from the hollow fibers. After connection as previously described, the dialyzers were rinsed with 0.5 L normal saline withdrawn from the 37° C. reservoir. After passing through the fibers, the 0.5 L saline was discharged to a drain. The dialyzers were then rinsed for 1,200 seconds with the 0.5 L normal saline remaining in the 37° C. reservoir, with the saline being returned to the reservoir after passing through the fibers. The dialyzers were then drained of any saline on the dialysate side to present excessive dilution of the plasma/maltodextrin solution.

Flow of the plasma/maltodextrin solution was then started through the fibers, with any liquid appearing at the venous blood port discharged to the drain until the plasma solution appeared at the port. Then, the plasma solution was recirculated to the 37° C. reservoir during continuous passage of the solution through the fibers. Such recirculation was continued for 60 minutes. Samples of the plasma and of filtrate through the fibers were taken at 20 minutes and 60 minutes, and analyzed using high-pressure liquid chromatography (HPLC) to determine the concentrations of various molecular-weight species of maltodextrin therein.

After 60 minutes, the experiment was stopped and all plasma solution was flushed from the dialyzers. The dialysate sides were emptied to the reservoir to prevent loss of low molecular-weight maltodextrin molecules.

Selected results of these experiments are shown in FIGS. 1–5.

Figure 1:
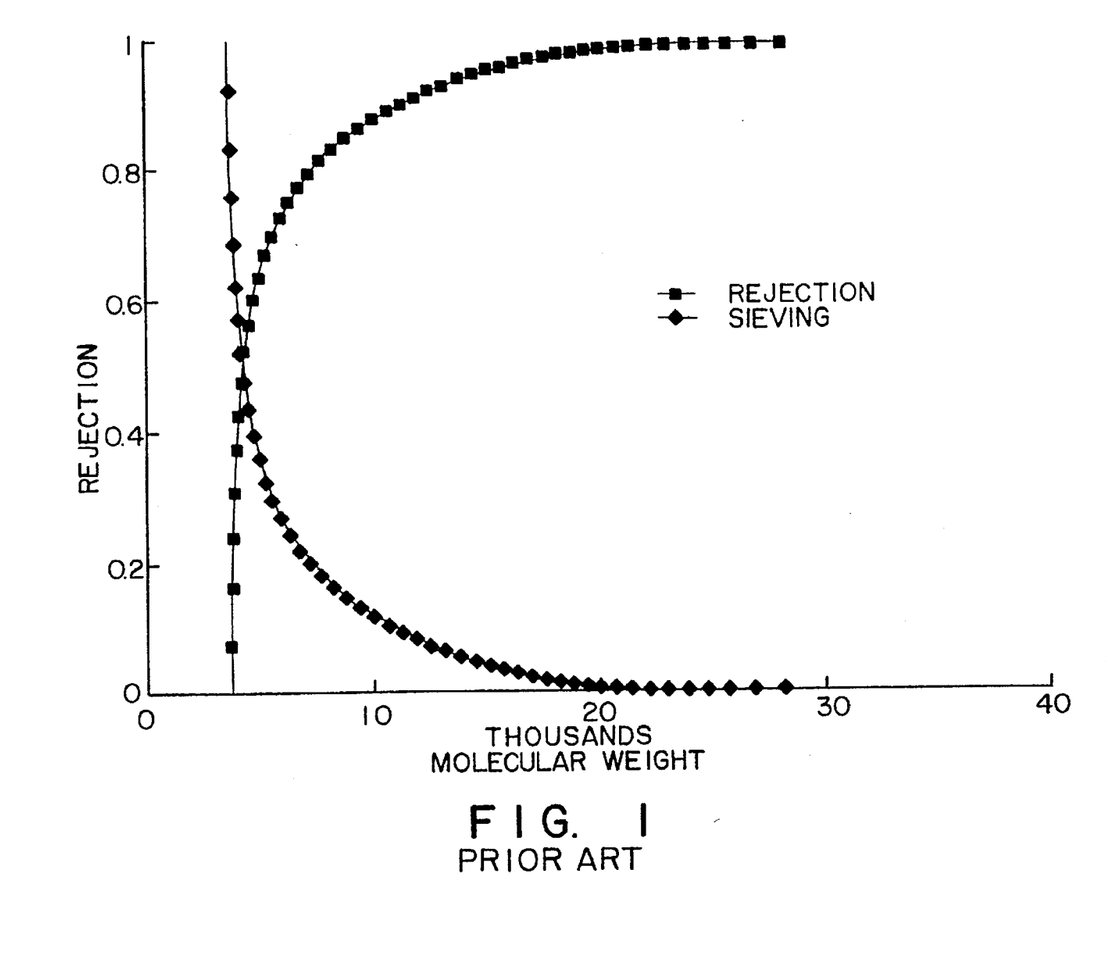
FIG. 1 is a profile of maltodextrin sieving and rejection behavior of a prior-art low-flux cellulose-acetate membrane, as discussed in Example 4.

FIG. 1 is a profile of the maltodextrin sieving and rejection behavior of a "CDAK 4000" dialyzer incorporating a prior-art low-flux cellulose-acetate-based membrane made by Althin CD Medical, Inc., Miami Lakes, Fla. In FIG. 1, the square-shaped points correspond to the ability of the membrane to reject (i.e., prevent passage therethrough of) maltodextrin molecules having particular molecular weights. The diamond-shaped points correspond to the ability of the membrane to sieve (i.e., pass therethrough) maltodextrin molecules.

As is known in the art, performance of hemofiltration membranes is typically described in terms of their ultrafiltration rates (mn/min/mmHg/m²) and their sieving properties. A suitable sieving statistic is determined by measuring the concentration of a solute (here, maltodextrin) in liquid on the "blood" side and on the "dialysate" side. The sieving statistic plotted in FIG. 1 is defined by $C_d/(C_b+C_d)$, wherein $C_d$=solute concentration on the dialysate side and $C_b$=solute concentration on the blood side. The rejection statistic plotted in FIG. 1 is defined by $C_b/(C_b+C_d)$.

Figure 2:
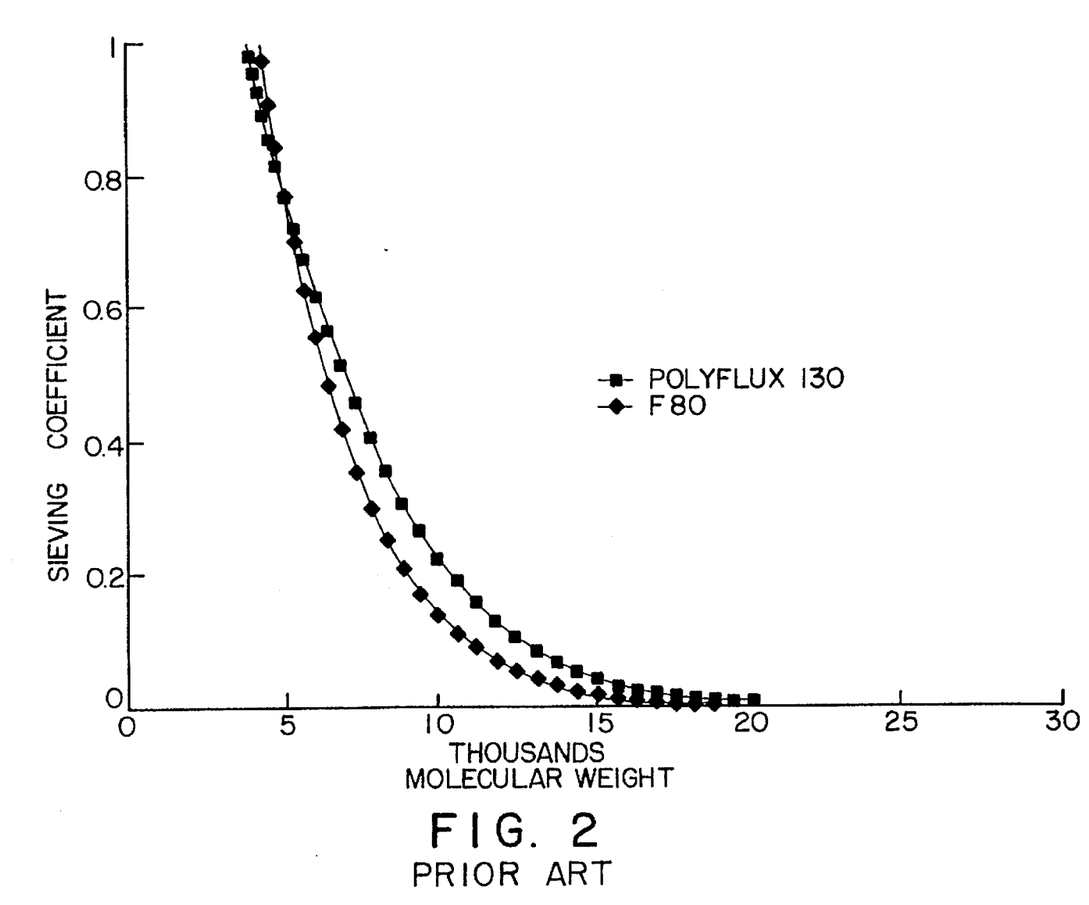
FIG. 2 shows maltodextrin sieving profiles for two prior-art hemodialysis membranes, as discussed in Example 4.

FIG. 2 shows maltodextrin sieving profiles for two prior-art hemodialysis membranes. The "sieving coefficient" axis (ordinate) represents values of the sieving statistic described above. In FIG. 2, the "Polyflux 130" membrane is a hydrophilic polyamide-based high-flux membrane manufactured by Gambro, Lund, Sweden; the "F80" membrane is a polysulfone membrane made by Fresenius.

Figure 3:
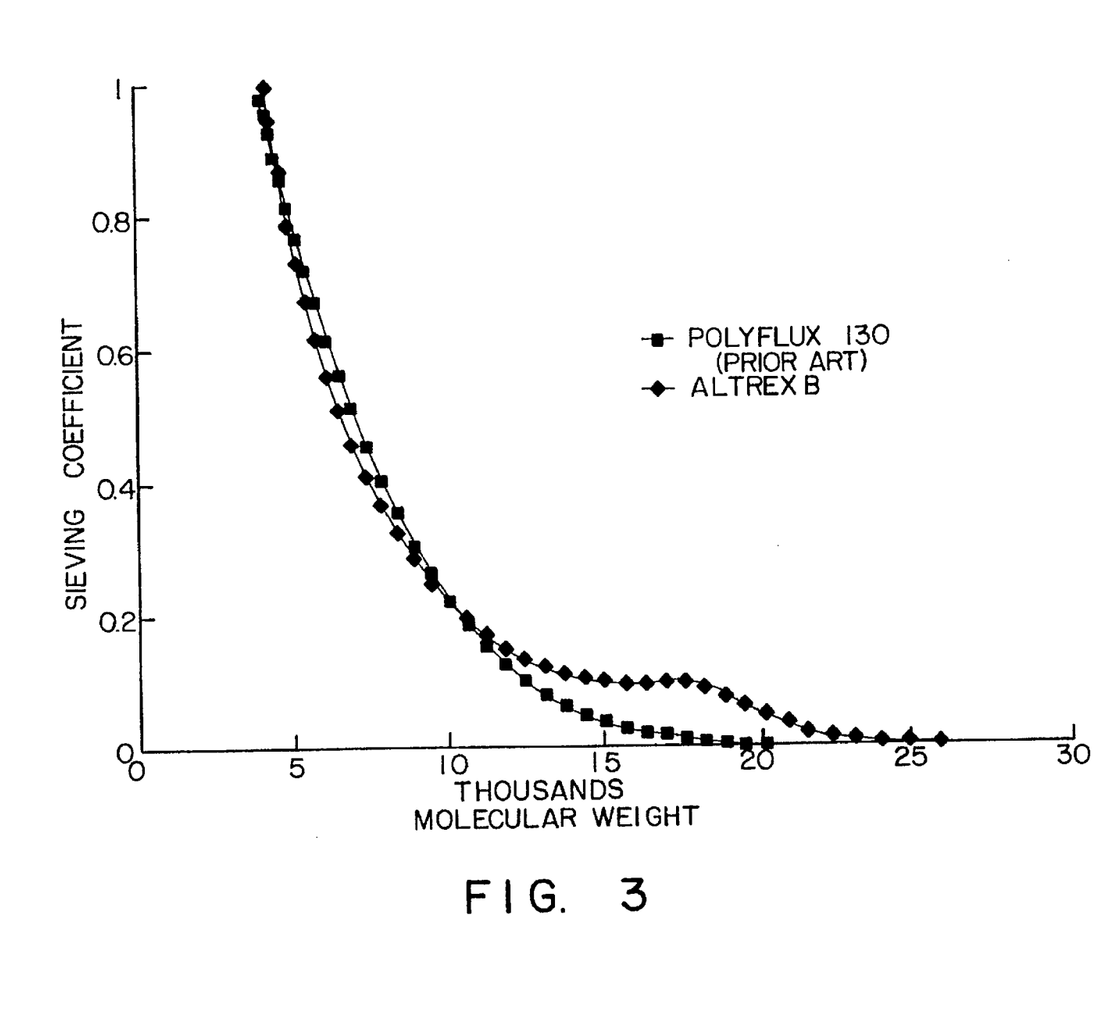
FIG. 3 is a comparative plot of the maltodextrin sieving profile of a prior-art "Polyflux 130" membrane, compared to a membrane according to the present invention, as discussed in Example 4.

FIG. 3 is a comparative plot of the maltodextrin sieving profiles of the prior-art "Polyflux 130" membrane and an "Altrex B" membrane according to the present invention.

Figure 4:
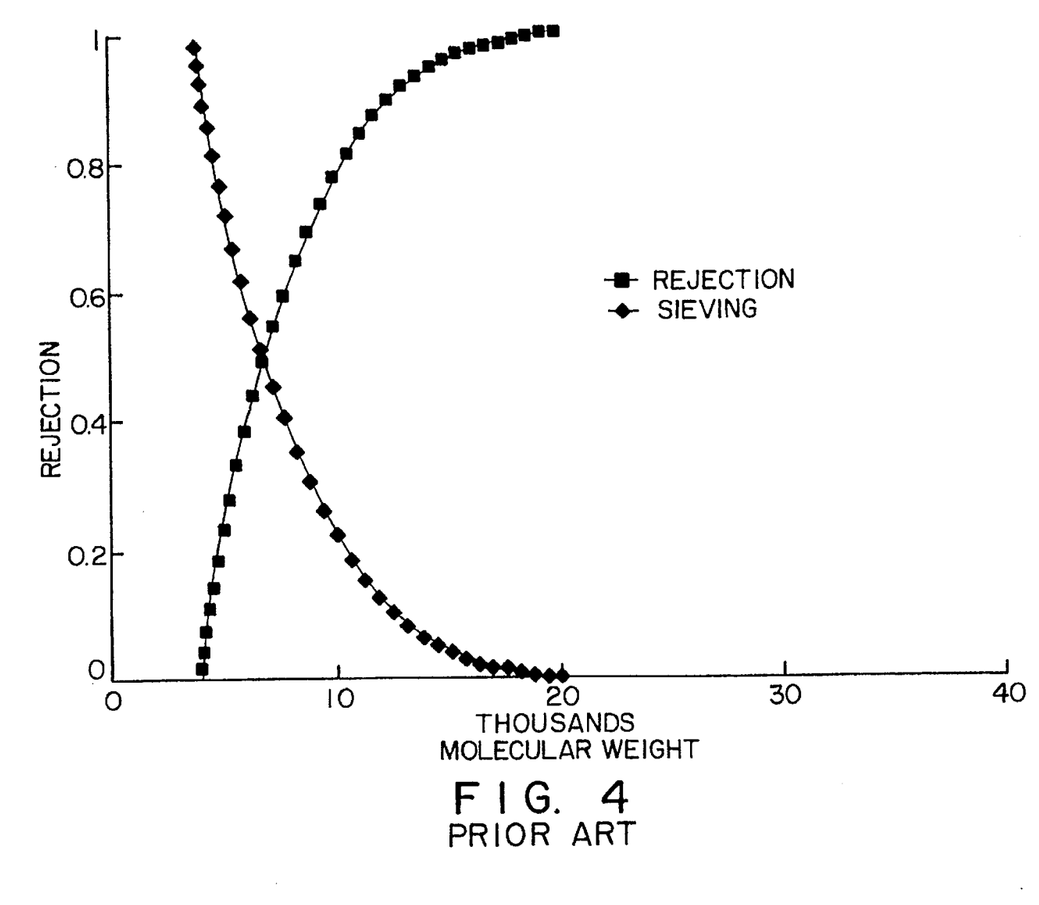
FIG. 4 shows sieving data for a prior-art "Polyflux 130" membrane as well as a plot of values of the corresponding rejection statistic for the prior-art membrane, as discussed in Example 4.

FIG. 4 shows, for the prior-art "Polyflux 130" membrane, the sieving data Shown in FIGS. 2 and 3. FIG. 4 also shows a plot of values of the corresponding rejection statistic for the "Polyflux 130" membrane.

Figure 5:
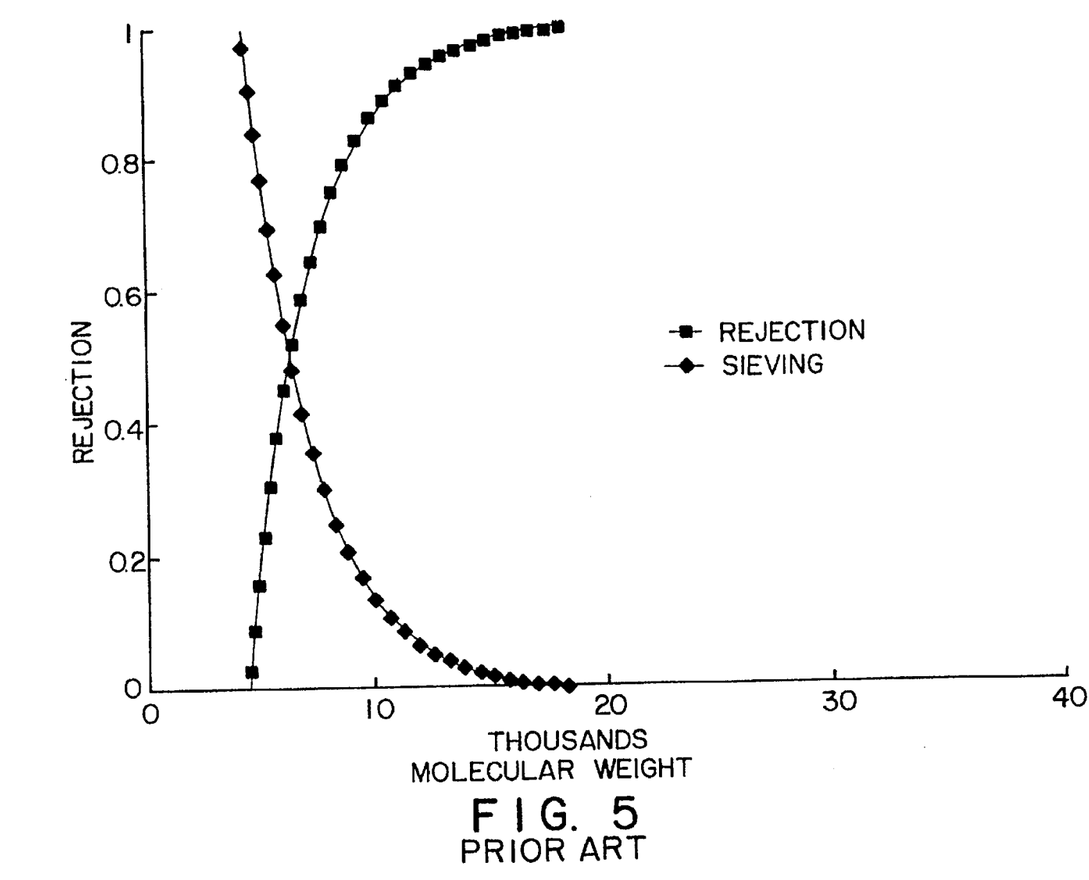
FIG. 5 shows plots of sieving and rejection statistics (for maltodextrin) for the prior-art "F80" membrane, as discussed in Example 4.

FIG. 5 shows, for the prior-art "F80" membrane, plots of the sieving and rejection statistics (for maltodextrin).

EXAMPLE 5

This Example is an investigation of in vivo clearance data of a cellulose acetate membrane according to the present invention. The data, shown in Table 4, were obtained using conventional methods using a hemodialyzer made with the fibers.

TABLE 4

| | In Vivo Clearance (cm/min) | | | | |
|---|---|---|---|---|---|
| $K_{uF}$* | Urea | Creatinine | Uric Acid | Phosphate | $K_{uF}$* |
| 50.0 | 182 | 150 | 155 | 147 | 16.9 |
| | 233 | 182 | 195 | 184 | |
| | 289 | 220 | 223 | 195 | |

*units: mL/hr/mmHg/m$^2$

What is claimed is:

1. A process for making a hollow-fiber semi-permeable membrane adapted for purifying aqueous biological liquids, the process comprising:
   (a) providing a molten liquid comprising 32 to 40% w/w of a cellulose acetate, 5 to 10% w/w glycerine, and 50 to 63% w/w polyethylene glycol;
   (b) extruding the molten liquid of step (a) through an annular spinneret to produce a hot hollow fiber, the fiber having a lumen diameter of about 175 to about 210 μm and a wall thickness of about 10 to about 35 μm;
   (c) cooling the hot hollow fiber of step (b); and
   (d) contacting the cooled hollow fiber of step (c) with water at a leach temperature of about 70° to about 85° C. so as to leach glycerine and polyethylene glycol from the fiber, thereby forming a hollow-fiber membrane made of a cellulosic material consisting of cellulose acetate and exhibiting a $K_{uF}$ of 15–55 mL/hr/mmHg/m$^2$.

2. A process as recited in claim 1 including the step, after step (b), of stretching the fiber longitudinally so as to increase its length by no greater than 20 percent.

3. A process as recited in claim 1 including the step, after step (d), of replasticizing the fiber.

4. A process as recited in claim 3 wherein the step of replasticizing the fiber comprises contacting the fiber with an aqueous glycerine solution.

5. The process of claim 1 wherein the molten liquid comprises 32.0 to 39.5% w/w cellulose acetate.

6. The process of claim 1 wherein the molten liquid comprises 32.0 to 39.0% w/w cellulose acetate.

7. The process of claim 1 wherein the molten liquid comprises 32.0 to 38.5% w/w cellulose acetate.

8. A process for making a hollow-fiber semi-permeable membrane adapted for purifying aqueous biological liquids, the process comprising:
   (a) providing a mixture consisting substantially of 32 to 40% w/w of a non-thrombogenic, non-toxic, thermoplastic, hydrophilic, cellulose acetate material having a melting temperature; 5 to 10% w/w of a water-miscible non-solvent for the cellulose acetate material; and 50 to 63% w/w of a water-miscible solvent for the cellulose acetate material, the non-solvent and the solvent being liquids at the melting temperature of the cellulose acetate material;
   (b) heating the mixture of step (a) to a temperature greater than the melting temperature of the cellulose acetate material and, while heating the mixture, mixing the mixture to homogeneity;
   (c) extruding the heated liquid of step (b) to produce a hot hollow fiber, the fiber having a lumen diameter of about 175 to about 210 μm and a wall thickness of about 10 to about 35 μm;
   (d) cooling the hot hollow fiber of step (c); and
   (e) contacting the cooled hollow fiber of step (d) with water at a leach temperature less than the melting temperature of the cellulose acetate material, the leach temperature being sufficient to leach the solvent and the non-solvent from the fiber, thereby forming a hollow-fiber membrane made of a cellulosic material consisting of cellulose acetate and exhibiting a $K_{uF}$ of 15 to 55 mL/hr/mmHg/m$^2$.

9. A process as recited in claim 8 wherein, in step (b), the mixture is heated to a temperature of about 165° to about 180° C.

10. A process as recited in claim 8 wherein the solvent is glycerine and the non-solvent is polyethylene glycol having a molecular weight of about 150 to about 600 daltons.

11. A hollow fiber semipermeable membrane produced by a process as recited in claim 8.

12. An extracorporeal blood-treatment device comprising hollow fibers as recited in claim 11.

13. A process for making a hollow-fiber semi-permeable membrane adapted for purifying aqueous biological liquids, the process comprising:
   (a) providing a substantially homogeneous mixture consisting substantially of 32 to 40% w/w of a cellulose acetate, 5 to 10% w/w glycerine, and 50 to 63% w/w polyethylene glycol having a molecular weight of about 150 to about 600 daltons, the mixture being at a temperature of about 165° to about 180° C. so as to melt the cellulose acetate;
   (b) extruding the mixture at said temperature through an annular spinneret to produce a hot hollow fiber, the fiber having an original length and being made of a cellulosic material consisting of cellulose acetate;
   (c) as the hot hollow fiber is extruded through the annular spinneret, cooling the hot hollow fiber so as to facilitate a thermally induced phase separation of the cellulose acetate in the fiber from the polyethylene glycol and the glycerine;
   (d) while cooling the hot hollow fiber, longitudinally stretching the hollow fiber so as to increase its length relative to the original length by no greater than about 20 percent, thereby further facilitating the thermally induced phase separation of cellulose acetate from the polyethylene glycol and the glycerine, and providing the hollow fibers with a lumen diameter of about 175 to about 210 μm and a wall thickness of about 10 to about 35 μm;
   (e) contacting the cooled hollow fiber of step (d) with water at a leach temperature of about 70° to about 85° C. so as to leach the glycerine and the polyethylene glycol from the cellulose acetate;
   (f) replasticizing the hollow fibers of step (e) by contacting the fibers with an aqueous solution comprising about 30 to about 40% w/w glycerins; and
   (g) removing water from the fibers of step (f) so as to confer on the fibers a glycerine concentration of about 45 to about 50% w/w and a water concentration of about 15 to about 18% w/w when the fibers are at equilibrium with the atmosphere, the fibers exhibiting a $K_{uF}$ of 15–55 mL/hr/mmHg/m$^2$.

14. A process as recited in claim 13 wherein, in step (g), water is removed from the fibers by drying the fibers in air at about 70° to about 80° C.

15. A hollow fiber semipermeable membrane produced by a process as recited in claim 13.

16. An extracorporeal blood-treatment device comprising hollow fibers as recited in claim 15.

* * * * *

UNITED STATES PATENT AND TRADEMARK OFFICE
CERTIFICATE OF CORRECTION

PATENT NO. : 5,643,452
DATED : July 1, 1997
INVENTOR(S) : ALTHIN ET AL.

It is certified that error appears in the above-identified patent and that said Letters Patent is hereby corrected as shown below:

Column 3, line 26, "follow" should be --hollow--.

Column 5, line 18, "See generally" should be --See generally--.

Signed and Sealed this

Seventeenth Day of March, 1998

Attest:

BRUCE LEHMAN

Attesting Officer           Commissioner of Patents and Trademarks